United States Patent
Hiiro et al.

(10) Patent No.: US 7,348,294 B2
(45) Date of Patent: Mar. 25, 2008

(54) ADSORBENT AND METHOD FOR ADSORBING CARDIAC GLYCOSIDE

(75) Inventors: Junko Hiiro, Akashi (JP); Shigeo Furuyoshi, Kobe (JP); Satoshi Takata, Takasago (JP); Shuichi Tsuruoka, Kawachi-gun (JP); Akio Fujimura, Kawachi-gun (JP)

(73) Assignee: Kaneka Corporation, Osaka-shi (JP)

( * ) Notice: Subject to any disclaimer, the term of this patent is extended or adjusted under 35 U.S.C. 154(b) by 227 days.

(21) Appl. No.: 10/276,293

(22) PCT Filed: May 23, 2001

(86) PCT No.: PCT/JP01/04307

§ 371 (c)(1),
(2), (4) Date: Jun. 17, 2003

(87) PCT Pub. No.: WO01/89602

PCT Pub. Date: Nov. 29, 2001

(65) Prior Publication Data

US 2004/0004041 A1    Jan. 8, 2004

(30) Foreign Application Priority Data

May 25, 2000    (JP) .............................. 2000-154956

(51) Int. Cl.
*B01J 20/22*    (2006.01)

(52) U.S. Cl. ..................................... 502/401

(58) Field of Classification Search ................ 502/400, 502/401, 407, 404
See application file for complete search history.

(56) References Cited

U.S. PATENT DOCUMENTS

| 3,909,357 A |   | 9/1975 | Reinhard et al. |
| 4,742,159 A | * | 5/1988 | Batz et al. ............... 530/389.8 |

FOREIGN PATENT DOCUMENTS

| EP | 0 819 439 A1 | 1/1998 |
| EP | 0 993 834 A1 | 4/2000 |
| JP | 5-253479 | 10/1993 |
| JP | 2001-114802 | 4/2001 |

OTHER PUBLICATIONS

Alexander, Christian et al., "Chemical Structure of Lipid A-The Primary Immunomodulatory Center of Bacterial Lipopolysaccharides", *Trends in Glycoscience and Glycotechnology*, vol. 14 No. 76 (Mar. 2002) p. 69.

Von Myoungki Baek, M.S., "Dynamic System Analysis of Receptor Interaction and Effectuation Mechanisms of Digoxin in the Rat Heart", (1970), see "Cardiac Glycosides", chapter 1.1, pp. 1-3.

* cited by examiner

*Primary Examiner*—Edward M. Johnson
(74) *Attorney, Agent, or Firm*—Kratz, Quintos & Hanson, LLP

(57) ABSTRACT

An adsorbent for cardiac glycoside contained in body fluid, comprising a compound having a log P value of at least 6 immobilized on a water-insoluble carrier is provided. A process for adsorbing and removing cardiac glycoside contained in body fluid efficiently, which comprises contacting body fluid with this adsorbent for cardiac glycoside is provided.

1 Claim, 3 Drawing Sheets

ADSORBENT AND METHOD FOR ADSORBING CARDIAC GLYCOSIDE

TECHNICAL FIELD

The present invention relates to an adsorbent for adsorbing and removing cardiac glycoside from body fluid, a process for adsorbing and removing cardiac glycoside and adsorber for cardiac glycoside.

BACKGROUND ART

Some steroid glycosides have a common chemical structure and acts on the heart with an effect of promoting its action. These glycosides are called cardiac glycoside, and contained in a wide variety of plants belonging to Liliaceae, Scrophularia and Apocynaceae. The cardiac glycoside strengthens the contraction of cardiac muscle directly and thus commonly used as an inotropic agent. Frequently used ones are digitoxin, digoxin, methyldigoxin, deslanoside, digilanides, ouabain and proscillaridin. Among them, those obtained from Scrophularia, such as digitoxin, digoxin, methyldigoxin, deslanoside and digilanides, are called digitalis and particularly widely used as an inotropic agent. And thus in some cases the term digitalis generically represents the cardiac glycosides in a broad sense.

Though cardiac glycosides are widely used as an inotropic agent, poisoning symptoms called digitalism are sometimes caused when used in an excessive amount. In the case of using cardiac glycoside such as digoxin which is excreted mainly through renal routes, a patient with impaired renal function is more likely to develop the digitalism. Examples of such symptoms are alimentary problems including loss of appetite, nausea, vomiting and diarrhea; visual impairment including xanthopsia, chloropsia and ambiopia; nervous system abnormalities including dizziness, headache, disorientation and mental derangement. In addition, more serious symptoms such as severe bradycardia, bigeminy, chaotic ventricular extrasystole and paroxysmal atrial tachycardia may be caused, sometimes developing into atrioventricular block, ventricular tachycardia or ventricular fibrillation.

When such toxic symptom appears, doses should be reduced or ceased, and medical treatment to alleviate the symptom becomes necessary. In the case of suffering from a serious symptom, desirable treatment is to lower the concentration level of the cardiac glycoside in body fluid rapidly. Preferable treatment for prompt level down of the cardiac glycoside concentration may be blood purification, but hemodialysis is generally considered of no effect. In addition, sufficient therapeutic effect cannot be obtained in some cases even by blood adsorption method with activated charcoal, which has been assumed to be most effective. For these reasons, a process for adsorbing and removing a larger amount of cardiac glycosides is desired.

The present invention has been made in order to solve the above problems.

An object of the present invention is to provide an adsorbent for adsorbing and removing cardiac glycoside from body fluid efficiently, a process for adsorbing and removing cardiac glycoside in body fluid and an adsorber for cardiac glycoside.

DISCLOSURE OF INVENTION

As a result of intensive studies on adsorbents capable of adsorbing and removing cardiac glycoside from body fluid efficiently, it has been found that an adsorbent comprising a water-insoluble carrier and a compound having a log P value of at least 6 immobilized on the carrier (P being a partition coefficient in an octanol-water system) can adsorb and remove cardiac glycoside from body fluid efficiently, and the present invention has been accomplished.

That is, the present invention relates to an adsorbent for cardiac glycoside contained in body fluid comprising a compound which is immobilized on a water-insoluble carrier and has a log P value of at least 6.

In a preferable embodiment, the water-insoluble carrier is a water-insoluble porous carrier.

In another preferable embodiment, the water-insoluble porous carrier has an exclusion limit for globular protein of at most 600,000.

Preferably, the cardiac glycoside is digitalis.

The present invention also relates to a process for adsorbing and removing cardiac glycoside contained in body fluid, which comprises contacting body fluid with an adsorbent for cardiac glycoside comprising a compound which is immobilized on a water-insoluble carrier and has a log P value of at least 6.

Furthermore, the present invention relates to an adsorber for cardiac glycoside which comprises a container having an inlet and an outlet for fluid and a means for preventing an adsorbent from flowing out of the container, wherein the adsorber is filled with the adsorbent for cardiac glycoside comprising a compound which is immobilized on a water-insoluble carrier and has a log P value of at least 6.

BEST MODE FOR CARRYING OUT THE INVENTION

Figure 1:
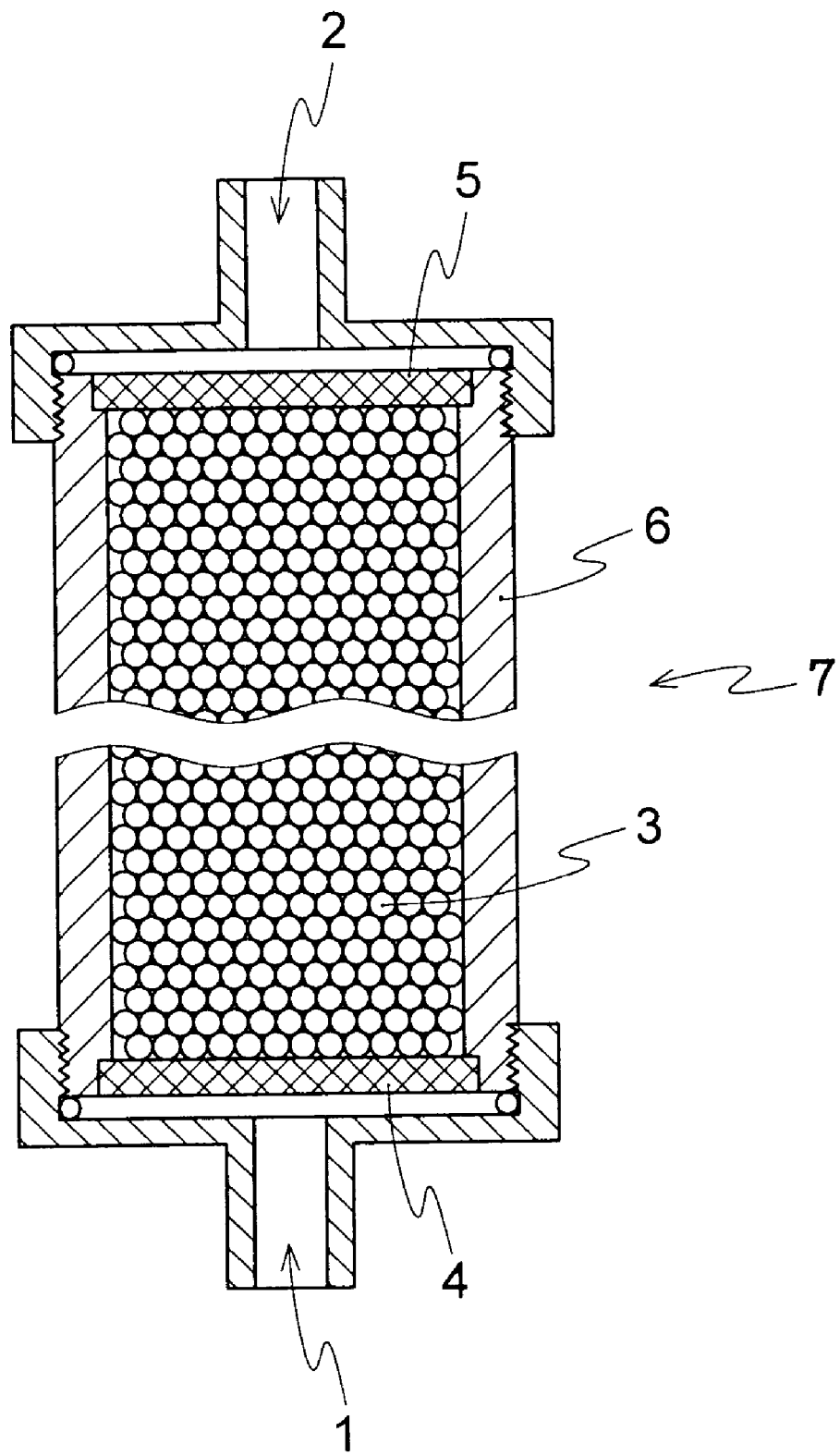
FIG. 1 is a schematic cross sectional view of an embodiment of the adsorber for cardiac glycoside of the present invention.

In the present invention, the cardiac glycoside refers to a series of steroid glycosides which have a common chemical structure and acts on the heart with an effect of promoting its action. The adsorbent of the present invention is particularly suitable for digitalis which is widely used among those glycosides. Digitalis is a cardiac glycoside obtained from Scrophularia, such as digitoxin, digoxin, methyldigoxin, deslanoside and digilanides.

Body fluid in the present invention includes blood, plasma, serum, ascites, lymph, arthral fluid and cerebrospinal fluid, fragments obtainable therefrom and other fluid components derived from living organs.

The adsorbent of the present invention comprises a compound having a log P value of at least 6 immobilized on a water-insoluble carrier. The log P value is a parameter which indicates the hydrophobic property of a compound. A typical partition coefficient P in an octanol-water system is determined as follows:

First, a compound is dissolved in octanol (or water), and an equal amount of water (or octanol) is added thereto. The mixture is shaken for 30 minutes with a Griffin flask shaker (made by Griffin & George Ltd.), and then centrifuged for 1 to 2 hours at 2,000 rpm. The respective concentrations of the compound in both octanol layer and water layer are measured by various methods such as spectroscopic method or GLC, and the partition coefficient is obtained by substituting the measured values into the following equation:

$$P = C_{oct}/C_w$$

$C_{oct}$: concentration of a compound in the octanol layer
$C_w$: concentration of a compound in the water layer Until now, many investigators have determined log P values of various compounds and the found values of the log P are put in order by C. Hansch et al ("PARTITION COEFFICIENTS AND THEIR USES"; Chemical Reviews, 71, page 525 (1971)).

As to compounds whose found values are unknown, calculated values (Σf) obtained by using a hydrophobic fragmental constant f shown in R. F. Rekker's book ("The HYDROPHOBIC FRAGMENTAL CONSTANT", Elsevier Sci. Pub. Corn., Amsterdam, 1977) can serve as a reference. The hydrophobic fragmental constants are values showing the hydrophobic property of various fragments determined by a statistical treatment of many found values of log P. It is reported that the sum of f values of respective fragments which constitute a compound approximately corresponds to the log P value of the compound. In the present invention, the definition of log P includes Σf.

In investigating compounds effective for adsorbing cardiac glycoside, compounds having various log P values were immobilized on a carrier. As a result, it has been found that the larger the log P value is, the greater the ability for adsorbing cardiac glycoside is. Specifically, it has been found that the ability of adsorbing cardiac glycoside is insufficient with compounds having a log P value of less than 6 but compounds having a log P value of at least 6, preferably at least 7 are effective for adsorbing cardiac glycoside. From these results, it is assumed that the adsorbing ability of the adsorbent for cardiac glycoside of the present invention is based on a hydrophobic interaction between cardiac glycoside and an atom group introduced onto a carrier by immobilization of a compound having a log P value of at least 6.

In the present invention, compounds to be immobilized onto the water-insoluble carrier can be used without particular limitation as long as they have a log P value of at least 6. However, in the case of immobilizing a compound onto the carrier by a chemical bonding method, part of the compound is often eliminated. When the eliminated group greatly contributes to the hydrophobic property of the compound, i.e., when the hydrophobic property of the atomic group immobilized onto the carrier becomes smaller than Σf=6 due to the elimination, it is not preferable to use the compound in the present invention from the viewpoint of the gist of the present invention.

Among compounds having a log P value of at least 6, preferable are compounds having a functional group which can be utilized for binding the compound to a carrier, such as unsaturated hydrocarbons, alcohols, amines, thiols, carboxylic acids and derivatives thereof, halides, aldehydes, hydrazids, isocyanates, compounds containing an oxirane ring such as glycidyl ethers, and halogenated silanes. Typical examples of these compounds are, for instance, amines such as hexadecylamine and octadecylamine; alcohols such as hexadecyl alcohol, and glycidyl ethers of these alcohols; carboxylic acids such as stearic acid and oleic acid, and their acid halides; carboxylic acid derivatives such as esters and amides; halides such as dodecyl chloride; thiols such as dodecanethiols and the like.

In addition to them, there can be used other compounds, e.g., compounds having a log P value of at least 6 selected from compounds in which a substituent containing a heteroatom such as halogen, nitrogen, oxygen or sulfur or other alkyl group, is substituted for hydrogen atom contained in the hydrocarbon moiety of the above exemplified compounds; and compounds having a log P value of at least 6 shown in the above-mentioned review by C. Hansch et al, "PARTITION COEFFICIENTS AND THEIR USES", Chemical Reviews, vol. 71, 525 (1971), tables on pages 555 to 613. However, compounds which can be used in the present invention are not limited to these compounds only.

These compounds may be used alone or in any combination of two or more. Further, these compounds may be used in combination with a compound having a log P value of less than 6.

The water-insoluble carrier in the adsorbent of the present invention means a carrier which is solid at ordinary temperature under ordinary pressure and is insoluble in water. The water-insoluble carrier in the present invention may be in the form of particle, board, fiber, hollow fiber and the like, but the form is not limited thereto. The size of the carrier is not particularly limited, but must be one such that enough space is given for cells contained in body fluid to pass through when the adsorbent of the present invention is packed in the column to be used.

For example, when the adsorbent of the present invention is in the form of particles, the average particle size is preferably 5 to 1,000 μm. When the average particle size is less than 5 μm, there is a possibility that enough space for cells contained in body fluid to pass through cannot be given. When the average particle size is more than 1,000 μm, there is a possibility that the adsorbing ability per volume is insufficient. When the adsorbent of the present invention is in the form of particles, the average particle size is more preferably 25 to 1,000 μm, most preferably 50 to 600 μm. In the range, from the viewpoint of preventing increase of the pressure drop, a sharp particle distribution is preferable. In addition, when the body fluid is blood, average particle diameter is at least 200 μm.

When the adsorbent of the present invention is in the form of hollow fiber, the inner diameter is preferably at least 1 μm, more preferably from 2 to 500 μm, most preferably from 5 to 200 μm. When the inner diameter is smaller than 1 μm, there is a possibility that body fluid containing cells do not pass through the adsorbent smoothly.

When the inner diameter is larger than 500 μm, there is a possibility that the adsorption ability per volume is insufficient.

Examples of water-insoluble carriers in the adsorbent of the present invention are inorganic carriers such as glass beads and silica gel; organic carriers comprising a synthetic polymer such as crosslinked polyvinyl alcohol, crosslinked polyacrylate, crosslinked polyacrylamide and crosslinked polystyrene, a polysaccharide such as crystalline cellulose, crosslinked cellulose, crosslinked agarose and crosslinked dextrin; and composite carriers obtained by combining the above materials, such as organic-organic carrier and organic-inorganic carrier.

Among these carriers, hydrophilic carriers are preferable since the non-specific adsorption does not easily occur and the adsorption selectivity for cardiac glycoside is excellent. The term "hydrophilic carrier" as herein used refers to a carrier whose contact angle for water is at most 60 degrees when the shape of the material constituting the carrier is flat plate. Various methods of measuring contact angle for water are known, and as shown in a book by Ikeda, Jikken Kagaku Sensho, Colloid Kagaku, Chapter 4, Thermodynamics of Interface, pages 75-104 (1986) published by Shokabo, Japan, the measuring method of putting water droplet on a flat-plate compound is most popular. Typical examples of a compound whose contact angle for water is at most 60 degrees as measured by this method are cellulose, polyvinyl alcohol, hydrolized ethylne-vinyl acetate copolymer, polyacrylamide, polyacrylic acid, polymethacrylic acid, methyl polymethacrylate, polyacrylic acid-grafting polyethylene, polyacrylamide-grafting polyethylene, glass and the like.

It is more preferable that these water-insoluble carriers have a large number of pores of an appropriate size, i.e., a porous structure. The carrier with a porous structure means a carrier comprising globular particles each of which is formed by agglomeration of microglobular particles of a macromolecular material and has spaces (macropores) formed between the agglomerated microglobular particles; a carrier comprising globular particles wherein each microglobular particle has pores; and a carrier which is made of a copolymer having a three-dimensional structure (polymer network) and which has pores (micropores) formed when swollen with an organic solvent having affinity with the copolymer.

From the viewpoint of adsorption ability per unit volume of the adsorbent, the porous water-insoluble carrier which is porous throughout the entire body rather than only in the surface region is preferable. A large pore volume and specific surface area are preferable as long as the adsorption property is not lost.

As for carriers satisfying these preferable conditions, porous cellulose carrier is an example. The porous cellulose carrier has the following advantages:
(1) since the porous cellulose carrier is tough and has relatively high mechanical strength, it is not easily destroyed or does not generate fine powder even by operation like agitation, and when packed in a column, compaction does not occur even if body fluid flows at a high flow rate, and in addition, the porous structure of the carrier is not easily affected from high pressure steam sterilization or the like;
(2) since the carrier comprises a cellulose, it is hydrophilic and there are a large number of hydroxyl groups which can be utilized for ligand bonding, and in addition, the non-specific adsorption does not easily occur;
(3) an adsorption capacity comparable to that of a soft carrier can be obtained because the carrier has a comparatively high strength even if the pore volume is increased; and
(4) the porous cellulose carrier is safer than synthetic polymer carriers.

Thus, the porous cellulose carrier is one of the most suitable carriers for the present invention. However, the carrier of the present invention is not limited thereto. In addition, the above carriers may be used alone or in combination of two or more.

From the viewpoint of adsorbing cardiac glycoside, which is a kind of steroid glycoside whose molecular weight is a few hundred to thousand, it is preferable that the water-insoluble carrier with porous structure has pores through which substances whose molecular weight is at least 1,000 can enter. On the other hand, from the viewpoint of safety, it is preferable that the water-insoluble carrier has a structure to prevent proteins in body fluid from entering the pore as much as possible. As for the standard of the molecular weight of a substance which can enter the fine pores, exclusion limit has been generally used. The term exclusion limit means the molecular weight of the smallest molecule among molecules which cannot pass through the pores (and excluded) in gel permeation chromatography as described in books (see, for example, Hiroyuki Hatano and Toshihiko Hanai, "Experimental High Performance Liquid Chromatography", Kagaku Dojin). In general, the exclusion limit of globular proteins, dextrans, polyethylene glycol and the like has been eagerly investigated. In the case of the exclusion limit of the carrier of the present invention, the values obtained by using globular protein are preferred.

When the exclusion limit of the carrier is more than 600,000, adsorption of proteins in body fluid (mainly albumin) increases, and thus the adsorbent becomes less practical from the viewpoint of safety. The exclusion limit for globular protein of the carrier used in the present invention is preferably at most 600,000, more preferably at most 300,000, and most preferably at most 100,000.

Further it is preferable that the carrier has a functional group which can be utilized in the reaction for immobilizing a ligand. Typical examples of functional group are hydroxyl group, amino group, aldehyde group, carboxyl group, thiol group, silanol group, amide group, epoxy group, halogen, succinimide group, acid anhydride group and the like, but the functional group is not limited thereto.

Both hard and soft carrier may be used as the carrier of the present invention. However, in the case of using the adsorbent for extracorporeal circulation, plugging must be prevented when the adsorbent is packed in the column to carry out the passing of fluid. For this purpose, sufficient mechanical strength is required for the carrier. Accordingly, it is more preferable to use a hard carrier in the present invention. The term "hard carrier" as used herein refers to, for example, in the case of a granulated carrier, a carrier which has a property that a linear relation between the pressure drop $\Delta P$ and flow rate is maintained up to a pressure drop of 0.3 kg/cm$^2$ when the carrier is uniformly charged in a cylindrical column and an aqueous fluid is passed through it, as in Reference Example described after.

The adsorbent of the present invention is obtained by immobilizing a compound having a log P value of at least 6 on a water-insoluble carrier. Various known methods of immobilization can be used without any particular limitation. However, when the adsorbent of the present invention is used for an extracorporeal circulation treatment, it is important from the viewpoint of safety to suppress the elimination or elution of ligand as much as possible in sterilization or treatment. For this purpose, it is preferable that the immobilization is conducted by the covalent bonding method.

In the adsorbent of the present invention, the amount of the compound immobilized is preferably 1 to 5,000 µmol/g– in wet weight, more preferably 10 to 3,000 µmol/g– in wet weight. This is because adsorption of cardiac glycoside tends to be insufficient when the amount of the compound immobilized is too small, while a component such as platelets may adhere to the adsorbent when the amount is too large and the body fluid is blood.

There are various processes for adsorbing and removing cardiac glycoside from body fluid by using the adsorbent of the present invention. The most convenient process is one such that body fluid is placed in a bag or the like and the adsorbent is mixed therewith so that cardiac glycoside is adsorbed, and then the adsorbent is filtered off to obtain body fluid from which cardiac glycoside has been removed. Another method is one in which the adsorbent is packed in a container having an inlet and an outlet for body fluid and equipped with a filter at the outlet, which can pass body fluid but cannot pass the adsorbent, and the body fluid is passed through the container. Both methods can be used, but the adsorbent of the present invention is suitable for the latter since the operation is simple and cardiac glycoside can be efficiently removed from body fluid of a patient, blood in particular, in on-line system by incorporating the method into an extracorporeal circulation circuit.

Figure 3:
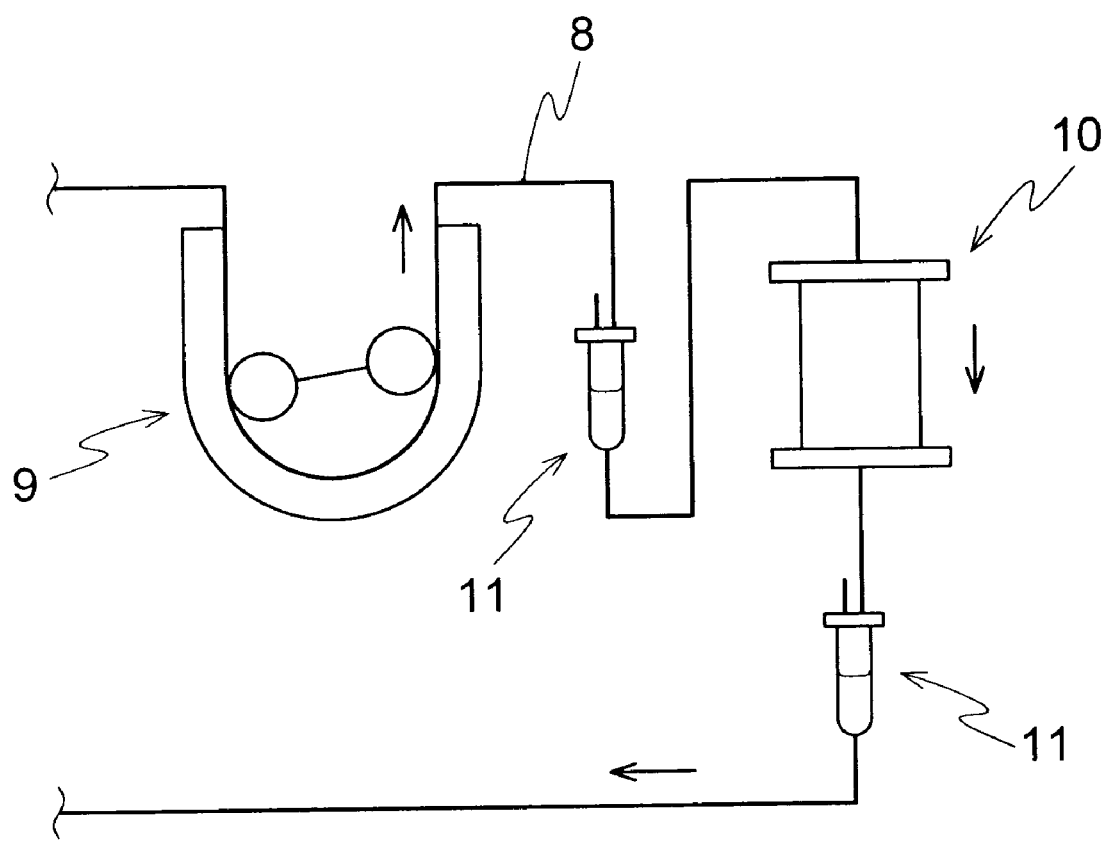
FIG. 3 is a view illustrating an extracorporeal circulation system in which a common blood purification device is set.

FIG. 3 is a view illustrating an extracorporeal circulation system in which a common blood purification device is set. In the figure, numeral 8 represents arterial circuit, numeral 9 represents a blood pump, numeral 10 represents blood purification device and numeral 11 represents drip chamber. Herein, as the blood purification device, the adsorber for cardiac glycoside of the present invention can be used.

In the extracorporeal circulation circuit as herein referred to, the adsorbent of the present invention can be used independently but also in combination with other extracorporeal circulation therapy systems. An example of other extracorporeal circulation therapy systems is dialysis therapy system.

The adsorber for cardiac glycoside of the present invention using the cardiac glycoside adsorbent mentioned above is explained below with reference to FIG. 1 which is a schematic section view illustrating an example of the adsorber. In FIG. 1, numeral 1 represents an inlet for body fluid, numeral 2 represents an outlet for body fluid, numeral 3 represents the cardiac glycoside adsorbent of the present invention, numerals 4 and 5 represent a filter (filter for preventing the adsorbent from flowing out) which can pass body fluid and components included therein but cannot pass the adsorbent, numeral 6 represents a column, and numeral 7 represents an adsorber for cardiac glycoside. The cardiac glycoside adsorber of the present invention is not limited to such an exemplified adsorber, and any device can be used as long as the device is one which comprises a container packed with an adsorbent and equipped with an inlet, an outlet for body fluid and a means for preventing spillage of the adsorbent.

Examples of means for preventing spillage of the adsorbent are filters such as mesh, non-woven fabric and cotton plug. Though there is no particular limitation for shape, material and size of the container, a cylindrical container is preferable regarding the shape. A material having sterilization resistance is preferable for the container. Examples thereof are silicone-coated glass, polypropylene, poly(vinyl chloride), polycarbonate, polysulfone, polymethylpentene and the like. Preferably, the capacity of the container is 50 to 1,500 ml, and the diameter is 2 to 20 cm. More preferably, the capacity of the container is 100 to 800 ml and the diameter is 3 to 15 cm. Most preferably, the capacity of the container is 100 to 400 ml and the diameter is 4 to 10 cm. When the volume of the container is less than 50 ml, the adsorbing amount is insufficient. And when the volume of the container is more than 1,500 ml, the extracorporeal circulation amount increases. Thus, these out-of-ranges are not preferable. The diameter of the container of less than 2 cm is not preferable because pressure drop is increased due to linear velocity growth. The diameter of more than 20 cm is not preferable because handling becomes difficult and yet the risk of coagulation arises due to linear velocity decline.

Hereinafter, the present invention is explained in detail by means of examples, but is not limited thereto.

REFERENCE EXAMPLE

Cylindrical glass columns (inner diameter 9 mm, length 150 mm) equipped with filters of a pore size of 15 µm at both ends were uniformly charged with each of an agarose gel (Biogel A-5m made by Bio-Rad Laboratories, U.S.A., particle size: 50 to 100 meshes), a vinyl polymer gel (TOYOPEARL HW-65 made by TOSOH Corporation, Japan, particle size: 50 to 100 µm) and a cellulose gel (CELLULOFINE GC-700m made by Chisso Corporation, Japan, particle size: 45 to 105 µm). The relationship between flow rate and pressure drop ΔP was determined by passing water through the column with a peristaltic pump. The results are shown in FIG. 2.

Figure 2:
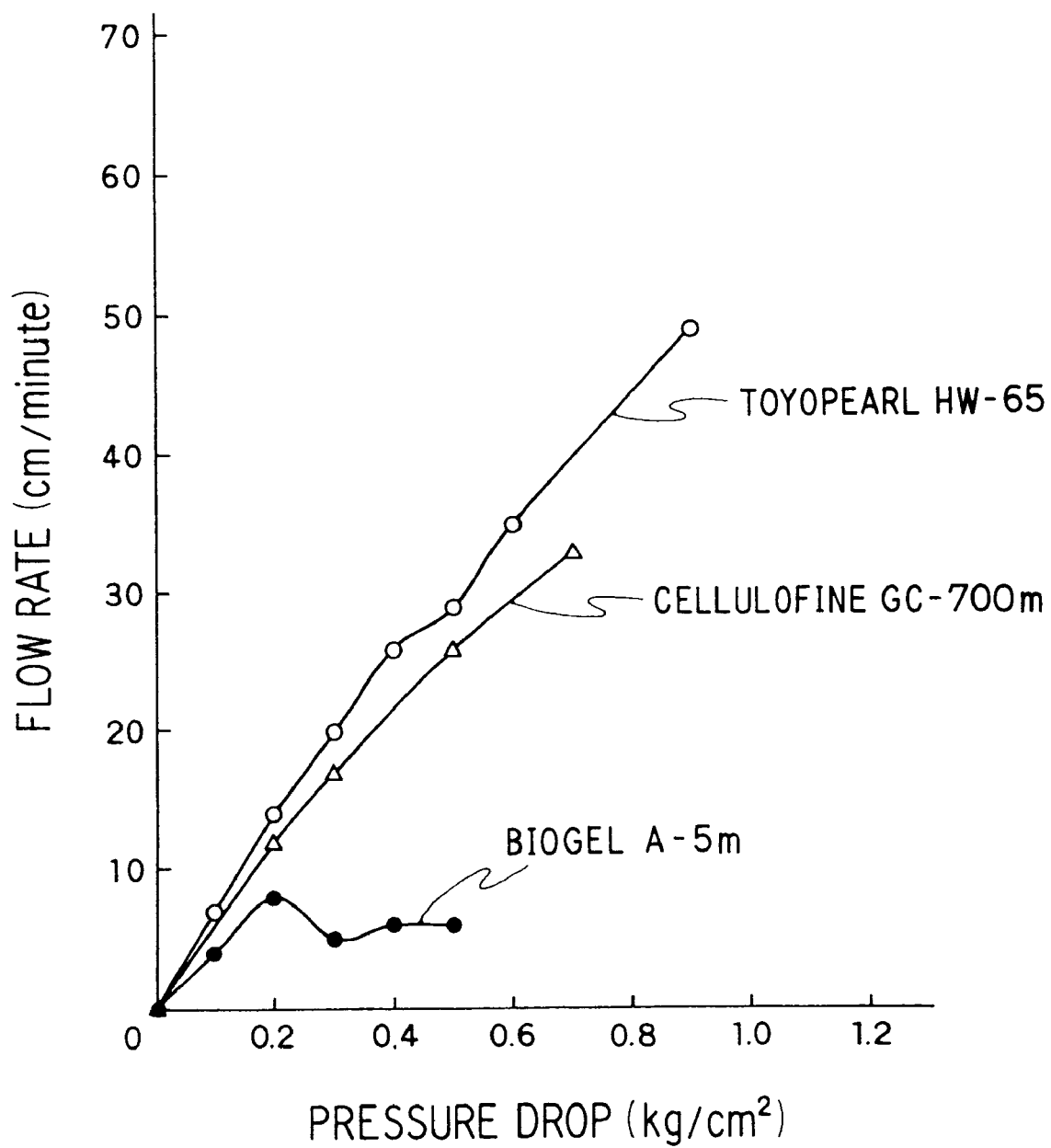
FIG. 2 is a graph illustrating relationships between the flow rate and pressure drop for three materials.

As shown in FIG. 2, it is found that the flow rate increases almost in proportion to the increase of pressure in the cases of TOYOPEARL HW-65 and CELLULOFINE GC-700m, whereas compaction is caused and the flow rate does not increase even if the pressure is increased in the case of Biogel A-5m. In the present invention, gels like the former materials which show linear relationship between the pressure drop ΔP and flow rate up to a pressure drop of 0.3 kg/cm$^2$ is called a hard gel.

Example 1

Commercially manufactured cellulose acetate in an amount of 1.4 kg was dissolved in a mixed solvent of 4.3 l of dimethyl sulfoxide and 4.3 l of propylene glycol. The solution was formed into droplets and coagulated in accordance with a method described in JP-A-63-117039 (oscillation method) to obtain 14 l of globular hydrogel particles of cellulose acetate.

To 1 l of these hydrogel particles was added an aqueous solution of sodium hydroxide to be 0.14 N, and the solution was mixed to carry out hydrolysis. Cellulose hydrogel particles (average particle size: 460 µm, exclusion limit for globular protein: 30,000) were obtained. Subsequently, the particles were reacted with 108 g of epichlorohydrin in a 0.4 N aqueous solution of sodium hydroxide, and with 8 g of n-hexadecylamine (Σf=7.22) in an aqueous solution of alcohol. Thus, 600 ml of globular cellulose hydrogel particles on which n-hexadecylamine was immobilized was obtained (amount of immobilized n-hexadecyl amine: 29 µmol/g– in wet weight).

To 0.4 ml of the thus-obtained adsorbent was added 2.4 ml of a normal human serum containing 5 ng/ml of digoxin. The mixture was incubated at 37° C. for 2 hours and the concentration of digoxin in the supernatant liquid was measured by the fluorescence polarization immunoassay (see Yuji Kagimoto et al, Journal of Hiroshima Prefectural Hospital, vol 17, p 87 to 92, 1985). The results are shown in Table 1.

Comparative Example 1

600 ml of n-dodecylamine-immobilized cellulose gel (amount of immobilized n-dodecylamine=27 µmol/g– in wet weight) was obtained in the same manner as in Example 1 except that n-hexadecylamine was changed to 11 g of n-dodecylamine (Σf=5.12). Adsorption test was carried out in the same manner as in Example 1 by using this adsorbent. The results are shown in Table 1.

Comparative Example 2

600 ml of n-octylamine-immobilized cellulose gel (amount of immobilized n-octylamine=28 µmol/g– in wet weight) was obtained in the same manner as in Example 1 except that n-hexadecylamine was changed to 9 ml of n-octylamine (log P=2.90). Adsorption test was carried out in the same manner as in Example 1 by using this adsorbent. The results are shown in Table 1.

Comparative Example 3

600 ml of n-butylamine-immobilized cellulose gel (amount of immobilized n-butylamine=32 µmol/g– in wet weight) was obtained in the same manner as in Example 1 except that n-hexadecylamine was changed to 5.5 ml of n-butylamine (log P=0.97). Adsorption test was carried out in the same manner as in Example 1 by using this adsorbent. The results are shown in Table 1.

Comparative Example 4

Adsorption test was carried out in the same manner as in Example 1 except for changing the adsorbent to DHP-1 (commercial name, activated charcoal available from Kuraray Co., Ltd.). The results are shown in Table 1.

TABLE 1

|  | Ligand | Concentration of digoxin in supernatant liquid |
| --- | --- | --- |
| Ex. 1 | n-hexadecylamine ($\Sigma f$ = 7.22) | 0.6 ng/ml |
| Com. Ex. 1 | n-dodecylamine ($\Sigma f$ = 5.12) | 3.3 ng/ml |
| Com. Ex. 2 | n-octylamine (log P = 2.90) | 4.3 ng/ml |
| Com. Ex. 3 | n-butylamine (log P = 0.97) | 4.2 ng/ml |
| Com. Ex. 4 | Adsorbent of activated carbon | 1.4 ng/ml |

Table 1 shows that the higher the log P value (or $\Sigma f$ value), the lower the concentration of the digoxin in the serum. The adsorbent obtained by immobilizing n-hexadecylamine whose log P value is at least 6 has an excellent adsorption ability for digoxin. It is shown that the adsorption ability for digoxin of this adsorbent is higher than that of DHP-1, the activated charcoal.

Example 2

A container (material: polypropylene) whose diameter is 5 cm and volume is 150 ml equipped with meshes (material: polyester) having openings of 150 μm on both the inlet and outlet of blood was charged with the globular hydrogel particles of n-hexadecylamine-immobilized cellulose obtained in Example 1. To the container was added 600 ppm of a buffer solution of citric acid and sodium citrate whose pH is adjusted to pH 6 to 6.5. High pressure steam sterilization was carried out at 121° C. for 20 minutes, and an adsorber for cardiac glycoside was prepared.

The prepared adsorber for cardiac glycoside was washed with 500 ml of saline containing 1 U/ml of heparin. A dog intramuscularly injected with 0.03 mg/kg of digoxin for 5 times every 12 hours was subjected to blood extracorporeal circulation at a rate of 50 ml/minute by using the adsorber shown as the blood purification device 10 in FIG. 3. In the extracorporeal circulation, 1000 U of heparin was intravenously injected at once at the beginning, and then heparin was continuously administrated into the vein at 1,000 U/hour. The concentrations of digoxin in blood before the extracorporeal circulation and after the lapse of 3 hours of extracorporeal circulation were measured in the same manner as in Example 1. The blood was taken from the upper part of the cardiac glycoside adsorber as shown in FIG. 3 after the extracorporeal circulation was carried out for 3 hours. The concentration of digoxin in blood was 5.27 ng/ml before the extracorporeal circulation but decreased to 1.03 ng/ml after three hours.

Comparative Example 5

A dog was subjected to blood extracorporeal circulation in the same manner as in Example 2 except that the blood purification device was changed to DHP-1 (commercial name, activated charcoal available from Kuraray Co., Ltd., cartridge volume: 200 ml). The concentration of digoxin in the blood was 5.28 ng/ml before the extracorporeal circulation but decreased to 2.66 ng/ml after 3 hours. It has been found that the concentration of digoxin in blood after the extracorporeal circulation was higher than that in the case of using the adsorber charged with n-hexadecylamine-immobilized adsorbent whose log P value was at least 6 (Example 2).

INDUSTRIAL APPLICABILITY

By using an adsorbent obtained by immobilizing a compound whose log P value is at least 6 on a water-insoluble carrier, cardiac glycoside in body fluid can be adsorbed and removed efficiently.

The invention claimed is:

1. A treating method for digitalism comprising adsorbing and removing cardiac glycoside contained in body fluid, which comprises contacting body fluid with an adsorbent for cardiac glycoside comprising a compound which is immobilized on a water-insoluble carrier and has a log P value of at least 6.

* * * * *